(12) United States Patent
Chiba et al.

(10) Patent No.: US 11,728,036 B2
(45) Date of Patent: Aug. 15, 2023

(54) STATE ESTIMATION DEVICE, METHOD AND PROGRAM

(71) Applicant: NIPPON TELEGRAPH AND TELEPHONE CORPORATION, Tokyo (JP)

(72) Inventors: Akihiro Chiba, Musashino (JP); Naoki Asanoma, Musashino (JP); Kazuhiro Yoshida, Musashino (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 329 days.

(21) Appl. No.: 17/272,917

(22) PCT Filed: Aug. 21, 2019

(86) PCT No.: PCT/JP2019/032590
§ 371 (c)(1),
(2) Date: Mar. 2, 2021

(87) PCT Pub. No.: WO2020/050026
PCT Pub. Date: Mar. 12, 2020

(65) Prior Publication Data
US 2021/0202108 A1    Jul. 1, 2021

(30) Foreign Application Priority Data
Sep. 4, 2018  (JP) .................. 2018-165088

(51) Int. Cl.
*G16H 50/30*      (2018.01)
*G16H 20/30*      (2018.01)
*G16H 40/60*      (2018.01)

(52) U.S. Cl.
CPC ............. *G16H 50/30* (2018.01); *G16H 20/30* (2018.01); *G16H 40/60* (2018.01)

(58) Field of Classification Search
CPC ......... G16H 50/30; G16H 20/30; G16H 40/60
(Continued)

(56) References Cited

U.S. PATENT DOCUMENTS 11,228,613 B2 *   1/2022   Chang .................... H04L 63/20
2015/0366518 A1*  12/2015  Sampson ............. A61B 5/7275
                                                              600/509
(Continued)

FOREIGN PATENT DOCUMENTS

JP        200934350 A      2/2009

OTHER PUBLICATIONS

Naoyuki Ebine et al., Comparative Study of Total Energy Expenditure in Japanese Men Using Doubly Labeled Water Method Against Activity Record, Heart Rate Monitoring, and Accelerometer Methods, Physical fitness science, vol. 51, No. 1, 2002, pp. 151-163.

*Primary Examiner* — Joy Chng
(74) *Attorney, Agent, or Firm* — Harness, Dickey & Pierce, P.L.C.

(57) ABSTRACT

In an embodiment of this invention, in a learning phase, a state estimation device acquires activity state data and biometric data at that time from user terminals of a plurality of users, generates a regression formula representing the relationship between the biometric data and the activity state data using a regression analysis method on the basis of these pieces of measurement data, and calculates a difference between the coefficients of the regression formula of all users and each user to generate a coefficient correction regression formula representing a relationship between the difference of the coefficient and an average value of the biometric data. In an estimation phase, the state estimation device acquires biometric data of a new user, corrects a coefficient value of an activity state estimation regression formula to a coefficient value for the new user on the basis (Continued)

of the average value of the biometric data and the coefficient correction regression formula, and estimates the activity state of the new user using the regression formula having the corrected coefficient.

6 Claims, 8 Drawing Sheets

(58) Field of Classification Search
USPC .......................................................... 705/2–3
See application file for complete search history.

(56) References Cited

U.S. PATENT DOCUMENTS

| | | | |
|---|---|---|---|
| 2016/0081620 A1* | 3/2016 | Narayanan | G01C 22/006 600/595 |
| 2017/0202486 A1* | 7/2017 | Martikka | A61B 5/02416 |
| 2018/0103859 A1* | 4/2018 | Provenzano | A61B 5/681 |
| 2018/0146907 A1* | 5/2018 | Nishiyama | A61B 5/1118 |

* cited by examiner

| USER 21 | |
|---|---|
| TIME POINT | BIOMETRIC DATA (HEART RATE/min) |
| 19:31 | 65 |
| 19:32 | 66 |
| 19:33 | 67 |
| 19:34 | 65 |
| 19:35 | 67 |
| 19:36 | 65 |
| 19:37 | 64 |

(a)

| USER 22 | |
|---|---|
| TIME POINT | BIOMETRIC DATA (HEART RATE/min) |
| 18:34 | 65 |
| 18:35 | 67 |
| 18:36 | 65 |
| 18:37 | 65 |
| 18:38 | 67 |
| 18:39 | 65 |
| 18:40 | 64 |

(b)

| USER 2N | |
|---|---|
| TIME POINT | BIOMETRIC DATA (HEART RATE/min) |
| 19:15 | 65 |
| 19:16 | 67 |
| 19:17 | 65 |
| 19:18 | 65 |
| 19:19 | 67 |
| 19:20 | 65 |
| 19:21 | 64 |

| USER 21 | |
|---|---|
| TIME POINT | STATE (ACTIVITY INTENSITY ml/kg/min) |
| 19:31 | 130 |
| 19:32 | 132 |
| 19:33 | 134 |
| 19:34 | 130 |
| 19:35 | 134 |
| 19:36 | 130 |
| 19:37 | 128 |

(a)

| USER 22 | |
|---|---|
| TIME POINT | STATE (ACTIVITY INTENSITY ml/kg/min) |
| 18:34 | 195 |
| 18:35 | 201 |
| 18:36 | 195 |
| 18:37 | 195 |
| 18:38 | 201 |
| 18:39 | 195 |
| 18:40 | 192 |

(b)

| USER 2N | |
|---|---|
| TIME POINT | STATE (ACTIVITY INTENSITY ml/kg/min) |
| 19:15 | 260 |
| 19:16 | 268 |
| 19:17 | 260 |
| 19:18 | 260 |
| 19:19 | 268 |
| 19:20 | 260 |
| 19:21 | 256 |

STATE ESTIMATION DEVICE, METHOD AND PROGRAM

CROSS-REFERENCE TO RELATED APPLICATIONS

This application is a 371 U.S. National Phase of International Application No. PCT/JP2019/032590 filed on Aug. 21, 2019, which claims priority to Japanese Application No. 2018-165088 filed on Sep. 4, 2018. The entire disclosures of the above applications are incorporated herein by reference.

TECHNICAL FIELD

This invention relates to a state estimation device, method, and program for estimating a physical activity state of a person on the basis of biometric data of the person, for example.

BACKGROUND ART

An index value representing a physical activity state during exercise such as a calorie consumption or an exercise intensity is useful information helpful in adjustment of an exercise time or an exercise load during weight training or an exercise for staying healthy. Such an index value is generally measured by an expensive dedicated apparatus. However, it is generally difficult for a general user who is not a professional sports player to use such an expensive apparatus.

Therefore, conventionally, a method of estimating an index value such as a calorie consumption or an exercise intensity on the basis of biometric data measured by a wearable sensor and using the same as a substitute has been proposed. For example, NPL 1 discloses a method of deriving a coefficient of a formula representing a relationship between biometric data and index values measured fro a plurality of users in advance and calculating an energy consumption corresponding to the biometric data measured by a new user using the coefficient.

CITATION LIST

Non Patent Literature

[NPL 1] Naoyuki Ebine, Mieko Shimada, Hiroaki Tanaka, Mamoru Nishimuta, Yutaka Yoshitake, Shinichi Saitoh, Peter J. H. Jones, "Comparative study of total energy expenditure in Japanese men using doubly labeled water method against activity record, heart rate monitoring, and accelerometer methods", *Tairyoku Kagaku*, Japanese Journal of Physical Fitness and Sports Medicine, vol. 51, no. 1, pp. 151-163, February 2002

SUMMARY OF THE INVENTION

Technical Problem

However, the biometric data measured by the wearable sensor has individual differences. Therefore, when the same coefficient is applied to all users to obtain the index value as in the method disclosed in NPL 1, since individual differences between users are not taken into consideration, it is difficult to estimate the index value indicating an activity state of a user with high accuracy.

This invention has been made in view of the above-described circumstances, and provides a technique for estimating an index value representing a state related to the mind and body of a user with high accuracy without measuring the same actually even when biometric data has individual differences between users.

Means for Solving the Problem

In order to solve the problems, in a first aspect of a state estimation device or method according to this invention, an index value representing an activity state of each of a plurality of users and biometric data measured in a period in which the activity is performed are acquired, an estimation formula which represents a relationship between the biometric data and the index value representing the activity state and which has a coefficient that takes an error between users, of the biometric data into consideration is generated on the basis of the biometric data and the index value representing the activity state and is stored. In this state, biometric data of an estimation target user is acquired, the coefficient of the estimation formula is corrected on the basis of the acquired biometric data of the estimation target user, and an index value representing an activity state corresponding to the acquired biometric data is estimated for the estimation target user on the basis of the estimation formula having the corrected coefficient.

Effects of the Invention

According to an aspect of this invention, it is possible to provide a technique for estimating an index value representing a state related to the mind and body of a user with high accuracy without measuring the same actually even when biometric data has individual differences between users.

BRIEF DESCRIPTION OF DRAWINGS

FIG. 6 is a diagram illustrating an example of a measurement result of a heart rate which is one of the biometric data of a plurality of users.

FIG. 7 is a diagram illustrating an example of a measurement result of an exercise intensity which is one of the activity states of a plurality of users.

DESCRIPTION OF EMBODIMENTS

Hereinafter, an embodiment according to this invention will be described with reference to the drawings.

EMBODIMENT

Configuration Example

Figure 1:
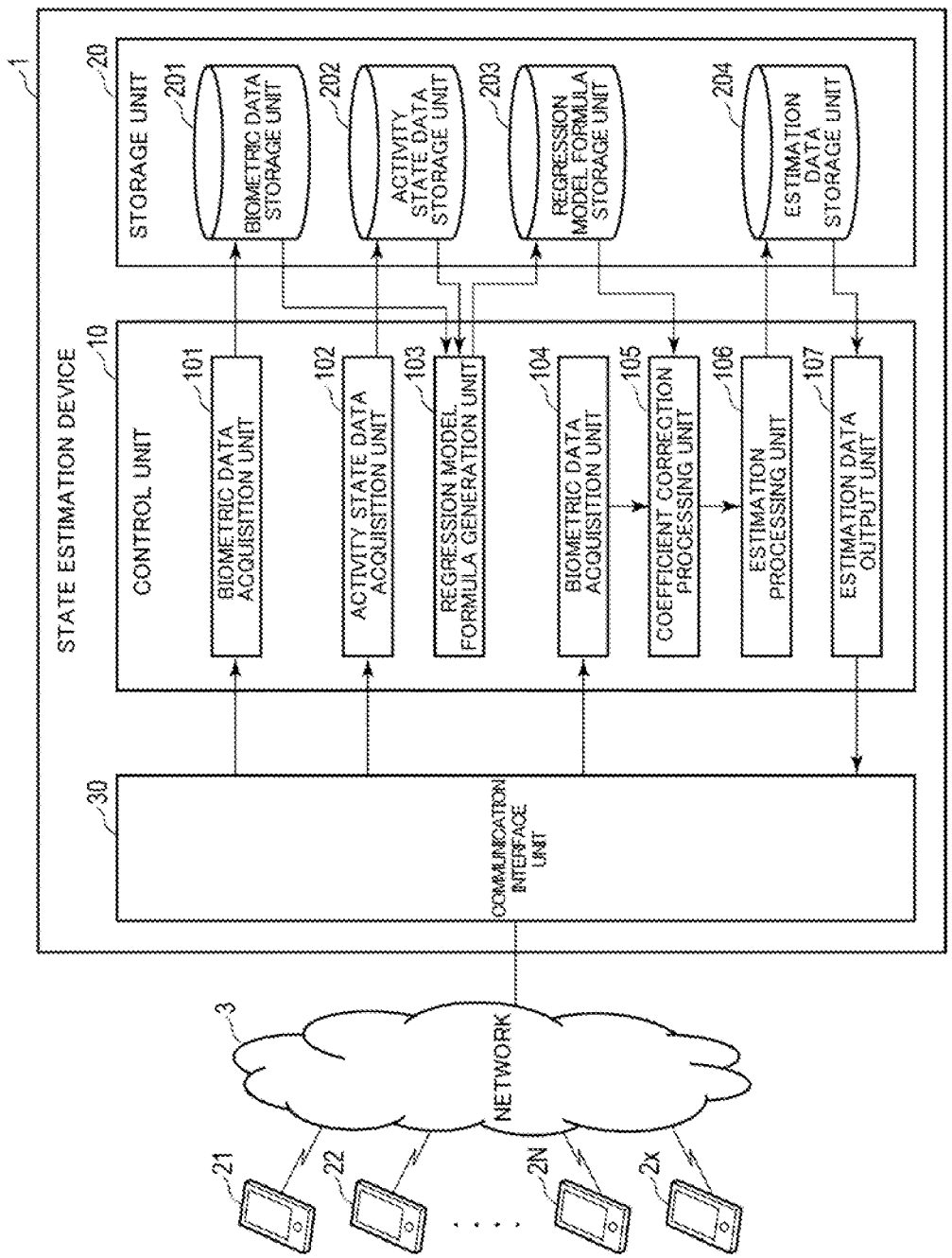
FIG. 1 is a block diagram illustrating a functional configuration of a state estimation device according to an embodiment of this invention.

FIG. 1 is a block diagram illustrating a functional configuration of a state estimation device according to an embodiment of this invention.

A state estimation device 1 is configured as a server computer or a personal computer, for example, and can communicate with a plurality of user terminals 21 to 2N and 2x via a network 3.

The user terminals 21 to 2N and 2x are held by different users and are configured as a smartphone, a tablet terminal, or a note-type personal computer, for example. The user terminals 21 to 2N and 2x have a function of receiving data representing an activity state and biometric data measured by an external measurement apparatus, for example, via a communication means or manual input and transmitting the same to the state estimation device 1 on a real-time basis or after temporarily storing the same.

The function of the user terminals 21 to 2N and 2x is realized by an application program installed in advance. Biometric sensors and wearable terminals having a communication function and a function of measuring an activity state can be used as the user terminals 21 to 2N and 2x.

A heart rate, a pulse rate, a blood pressure, and a blood-sugar level, for example, are used as the biometric data. These pieces of biometric data can be measured by a heart rate sensor, a pulse wave sensor, a blood pressure gauge, and a sensor for measuring a blood-sugar level, for example. An exercise intensity, a calorie consumption, a maximum oxygen intake, and an activity can be used as the data representing an activity state, for example. Such data representing the activity state can be computed on the basis of the measurement values of an oxygen intake measurement device, an activity meter, and a pulse oximeter (arterial oxygen saturation: SPO2), for example. For example, the exercise intensity can be calculated as the amount of oxygen consumed inside the body per unit weight in one minute.

The network 3 includes a public network such as the Internet and an access network for accessing the public network, for example. Although a local area network (LAN) or a wireless LAN, for example, is used as the access network, a wire telephone network, a cable television (CATV) network, a cellular network, and the like may be used beside the LANs.

The state estimation device 1 is operated by a medical institution, a health support center, a fitness club, or other health support providers, for example, and is configured as a server computer or a personal computer, for example. Although the state estimation device 1 may be installed alone, the state estimation device 1 may be installed, as one of its extended functions, in a terminal of a medical worker such as a doctor, an electronic medical records (EMR) server installed in each medical institution, an electronic health records (EHR) server installed in access characteristic region including a plurality of medical institutions, a cloud server of a service provider, and the like. Moreover, the state estimation device 1 may be installed in the user terminals 21 to 2N and 2x themselves as one of its extended functions.

The state estimation device 1 includes a control unit 10, a storage unit 20, and a communication interface unit 30. The communication interface unit 30 transmits data to the user terminals 21 to 2N and 2x via the network 3. Moreover, the communication interface unit 30 may have a function of transmitting data to a management terminal (not illustrated) connected via a LAN or a signal cable.

The storage unit 20 is a storage medium and is configured as a combination of a nonvolatile memory in which data can be written and read as necessary such as a hard disk drive (HDD) or a solid state drive (SSD), a nonvolatile memory such as a read only memory (ROM), and a volatile memory such as a random access memory (RAM), for example. The storage unit 20 has a program storage area and a data storage area. Programs necessary for executing various control processes according to an embodiment of this invention are stored in the program storage area are stored in the program storage area.

A biometric data storage unit 201, an activity state data storage unit 202, a regression model formula storage unit 203, and an estimation data storage unit 204 are provided in the data storage area. The biometric data storage unit 201 is used for storing the biometric data of each user acquired from the user terminals 21 to 2N in the learning phase. The activity state data storage unit 202 is used for storing data representing the activity state of each user acquired from the user terminals 21 to 2N in the learning phase. The regression model formula storage unit 203 is used for storing regression model formulas generated in the learning phase. The estimation data storage unit 204 is used for storing estimation data of the activity state calculated in the estimation phase.

The control unit 10 includes a hardware processor such as a central processing unit (CPU), for example, and includes, as a control function for realizing an embodiment of this invention, a learning biometric data acquisition unit 101, a learning activity state data acquisition unit 102, a regression model formula generation unit 103, an estimation biometric data acquisition unit 104, a coefficient correction processing unit 105, an estimation processing unit 106, and an estimation data output unit 107. These control functional units are realized by causing the hardware processor to execute the programs stored in the program storage area.

The learning biometric data acquisition unit 101 performs a process of acquiring the biometric data of each user from the user terminals 21 to 2N via the network 3 and the communication interface unit 30 and storing the same in the biometric data storage unit 201 in the learning phase. The biometric data is represented as data in which measurement values are correlated with measurement time points upon every measurement timing, for example.

The learning activity state data acquisition unit 102 performs a process of acquiring the data representing the activity state of each user from the user terminals 21 to 2N via the network 3 and the communication interface unit 30 and storing the same in the activity state data storage unit 202 in the learning phase. The activity state data is also represented as data in which measurement values are correlated with measurement time points upon every measurement timing, for example.

The regression model formula generation unit 103 generates a regression model formula representing a relationship between the biometric data and the activity state of all users and a relationship between the biometric data and the activity state of each user on the basis of the biometric data of each user stored in the biometric data storage unit 201 and the activity state data stored in the activity state data storage unit 202 in the learning phase. Moreover, the regression model formula generation unit 103 generates a formula for calculating a difference between the coefficient of each user and the coefficient of all users from the generated regression model formula of all users and the generated regression model formula of each user. Furthermore, the regression model formula generation unit 103 generates a regression model formula indicating a relationship between a difference in the coefficient and the average value of the biometric data of each user according to regression analysis. The regression model formula generation unit 103 performs a process of storing the generated regression model formulas in the regression model formula storage unit 203. A specific example of the regression model formula generation process will be described later.

The estimation biometric data acquisition unit 104 performs a process of acquiring the biometric data of an estimation target user of the activity state from the user terminal 2x held by the user via the network 3 and the communication interface unit 30 in the estimation phase. In this case, the biometric data is represented as data in which measurement values are correlated with measurement time points.

The coefficient correction processing unit 105 performs a process of generating a regression model formula in which the coefficient is corrected according to the biometric data of the estimation target user on the basis of the biometric data of the estimation target user and the regression model formula stored in the regression model formula storage unit 203.

The estimation processing unit 106 performs a process of estimating an activity state of the estimation target user corresponding to the acquired biometric data of the estimation target user using the regression model formula of which the coefficient is corrected and storing the estimation result in the estimation data storage unit 204.

The estimation data output unit 107 performs a process of transmitting data representing the estimation result stored in the estimation data storage unit 204 from the communication interface unit 30 to the user terminal 2x of the estimation target user via the network 3.

Operation Example

Next, an operation example of the state estimation device 1 configured in the above-described manner will be described.
(1) Learning Phase When a learning phase is set, the state estimation device 1 executes a learning process for generating a regression model formula as follows.

Figure 2:
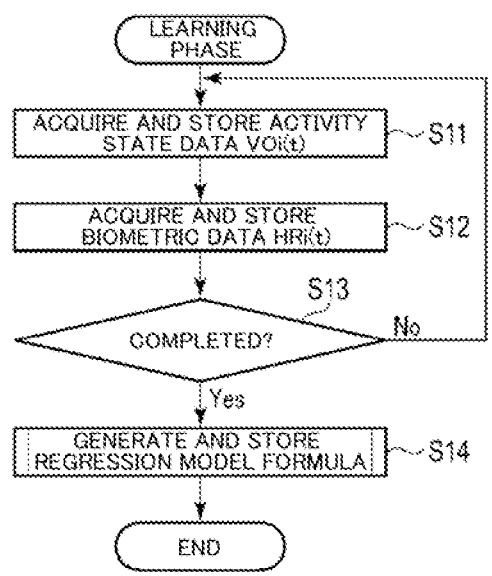
FIG. 2 is a flowchart illustrating the procedure and the content of the processing in a learning phase by the state estimation device illustrated in FIG. 1.

FIG. 2 is a flowchart illustrating an example of the procedure and the content of the processing in the learning phase by the control unit 10 of the state estimation device 1.

(1-1) Acquisition of Learning Training Data

A plurality of users cooperating in providing learning training data wears a biometric data measurement apparatus and an activity state measurement apparatus. For example, the users wear a wrist-watch measurement apparatus having a heart rate sensor or a pulse wave sensor incorporated therein or a garment-type measurement apparatus in which fiber has a heart rate sensing function as the biometric data measurement apparatus. On the other hand, the users wear an apparatus for measuring an oxygen intake as the activity state measurement apparatus, for example.

When the user performs exercise, for example, in this state, data representing the biometric data and the activity state of each user is measured every prescribed time intervals (for example, every minute) by the measurement apparatuses and the measurement data is transmitted to the user terminals 21 to 2N. A wireless interface which employs low-power wireless data communication standards such as Bluetooth (registered trademark), for example, is used as means for transmitting the measurement data from the measurement apparatuses to the user terminals 21 to 2N.

A heart rate per minute, for example, is measured as the biometric data. An oxygen intake per minute, for example, is measured as the activity state data. The user terminals 21 to 2N store the heart rate measurement data transmitted from the measurement apparatuses in internal memories as the biometric data of the users. Moreover, the user terminals 21 to 2N calculates exercise intensities of the users on the basis of the oxygen intakes per minute transmitted from the measurement apparatuses and stores the exercise intensities in the internal memories as the activity state data. The exercise intensity is calculated as the amount of oxygen per unit weight consumed inside the user's body in one minute. The biometric data and the activity state data measured by the measurement apparatuses may be manually input by the users of the user terminals 21 to 2N.

In the above description, a case in which the data measured by the measurement apparatuses is transmitted or manually input to the user terminals 21 to 2N has been described as an example. However, when the user terminal 21 to 2N themselves have a measurement function, the user terminals 21 to 2N measure the activity state data and the biometric data and stores the measurement data in the internal memories. In this case, the activity state data only may be manually input by the user.

First, in step S11, the control unit 10 of the state estimation device 1 accesses the user terminals 21 to 2N sequentially under the control of the activity state data acquisition unit 102 and receives the activity state data with the aid of the communication interface unit 30 via the network 3. The received activity state data is stored in the activity state data storage unit 202. FIG. 7 illustrates an example of the activity state data (exercise intensities per minute) acquired from the user terminals 21, 22, and 23 as an example of the activity state data acquired in the above-described manner. As illustrated in the drawing, the activity state data is stored in correlation with information representing a measurement time.

Subsequently, in step S12, the control unit 10 of the state estimation device 1 accesses the user terminals 21 to 2N sequentially under the control of the biometric data acquisition unit 101 and receives the biometric data with the aid of the communication interface unit 30 via the network 3. The received biometric data is stored in the biometric data storage unit 201. FIG. 6 illustrates an example of the biometric data (heart rates per minute) acquired from the user terminals 21, 22, and 23 as an example of the biometric data acquired in the above-described manner. As illustrated in the drawing, the biometric data is stored in correlation with information representing the measurement time.

The control unit 10 of the state estimation device 1 determines in step S13 whether acquisition of the activity state data and the biometric data from all user terminals 21 to 2N has been completed. When a user terminal from which the data has not been acquired remains, processes of steps S11 and S12 are executed repeatedly. When acquisition of the measurement data from all user terminals 21 to 2N is completed, the flow proceeds to a regression model formula generation process.

The control unit 10 of the state estimation device 1 may acquire the activity state data and the biometric data collectively a set of measurement data when accessing the user terminals 21 to 2N rather than acquiring the pieces of data separately. In the above description, a case in which the state estimation device 1 accesses the user terminals 21 to 2N to acquire the activity state data and the biometric data has been described as an example. However, the user terminals 21 to 2N may transmit the activity state data and the biometric data to the state estimation device 1 at arbitrary timings.

(1-2) Generation of Regression Model Formula

Subsequently, in step S14, the control unit 10 of the state estimation device 1 executes a learning process for generating the regression model formula under the control of the regression model formula generation unit 103 as follows.

Figure 3:
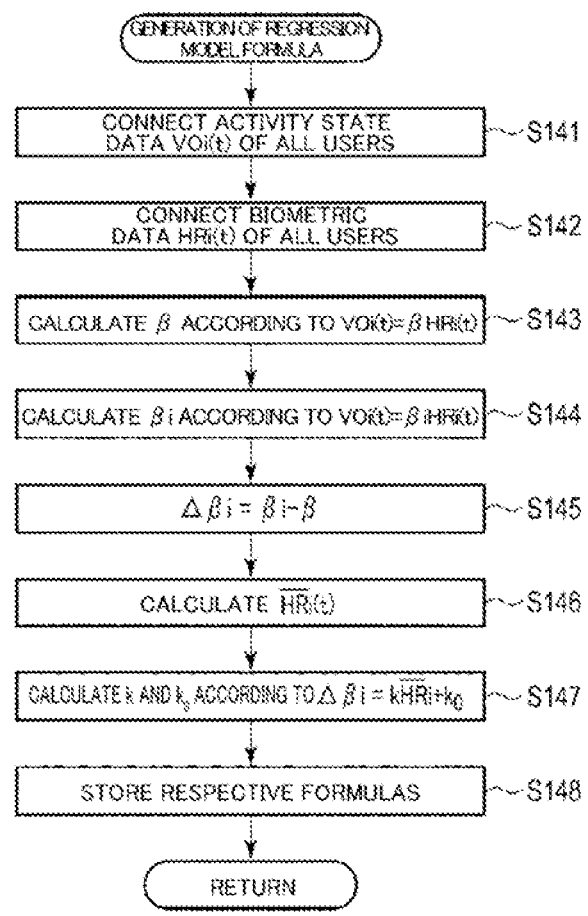
FIG. 3 is a flowchart illustrating the procedure and the content of a regression model formula generation process in the learning phase illustrated in FIG. 2.

FIG. 3 is a flowchart illustrating the processing procedure and the processing content. In the following description, activity state data (exercise intensity) and biometric data (heart rate) measured at time t of a user i (i=1 to N) are defined as VOi(t) and HRi(t), respectively.

That is, first, in step S141, the regression model formula generation unit 103 reads the activity state data VOi(t) of all users corresponding to the user terminals 21 to 2N from the activity state data storage unit 202 and connects the read data. Moreover, similarly, in step S142, the regression model formula generation unit 103 reads the biometric data HRi(t) of all users corresponding to the user terminals 21 to 2N stored in the biometric data storage unit 201 and connects the read data.

Subsequently, in step S143, the regression model formula generation unit 103 applies a regression analysis method on the basis of the connected activity state data VOi(t) of all users and the connected biometric data HRi(t) of all users to generate a regression formula below representing the relationship and calculates a coefficient $\beta$.

$$VOi(t) = \beta HRi(t) \quad (1)$$

Subsequently, in step S144, the regression model formula generation unit 103 applies a regression analysis method on the basis of the activity state data VOi(t) of each user i and the biometric data HRi(t) of all users to generate a regression formula below representing the relationship and calculates a coefficient $\beta i$.

$$VOi(t) = \beta i HRi(t) \quad (2)$$

In step S145, the regression model formula generation unit 103 calculates a difference $\Delta \beta i$ between the coefficient $\beta$ of all users and the coefficient $\beta i$ of each user calculated by Formulas (1) and (2) according to the following formula.

$$\Delta \beta i = \beta i - \beta \quad (3)$$

Subsequently, in step S146, the regression model formula generation unit 103 calculates an average value of the biometric data HRi(t) of the user i. The average value will be represented as $HRi^-$. Subsequently, in step S147, the regression model formula generation unit 103 applies a regression analysis method on the basis of the difference $\Delta \beta i$ of the coefficients calculated by Formula (3) and the average value $HRi^-$ of the biometric data to generate a regression formula below and calculates coefficients k and k0.

$$\Delta \beta i = k HRi^- + k0 \quad (4)$$

Figure 8:
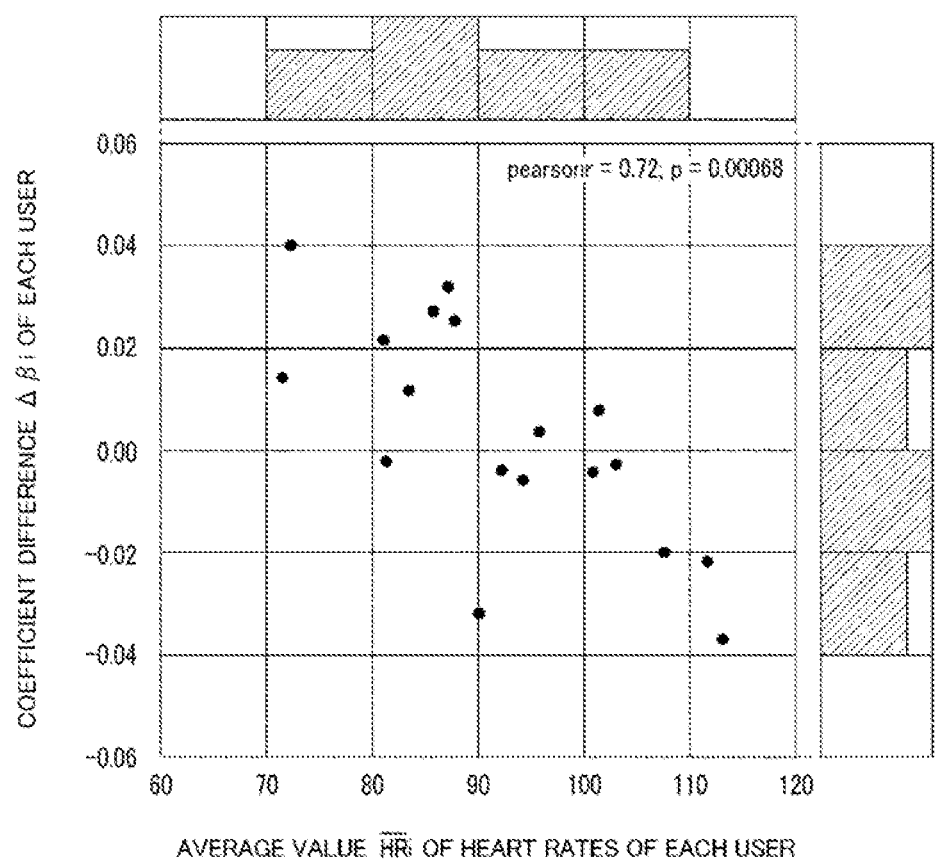
FIG. 8 is a diagram illustrating an example of a relationship between an average value of heart rates of respective users and a coefficient difference.

FIG. 8 is a diagram illustrating an example of a relationship between the average value $HRi^-$ of the heart rates of each user i and the difference $\Delta \beta i$ of the coefficients. As illustrated in FIG. 8, the relationship between the average value $HRi^-$ of the heart rates of each user i and the difference $\Delta \beta i$ of the coefficients shows a generally linear relation. That is, the relationship between the average value $HRi^-$ of the heart rates and the difference $\Delta \beta i$ of the coefficients can be represented as a linear regression formula as described above.

Finally, in step S148, the regression model formula generation unit 103 stores the regression formulas generated in the above-described processes in the regression model formula storage unit 203. Although all regression formulas may be stored, the coefficients $\beta$, $\beta i$, k, and k0 only of the regression formulas may be stored. In this way, the learning process for generating the regression model formula ends.

(2) Estimation Phase

When the learning of the regression model formula ends, the state estimation device 1 can thereafter estimate the activity state of a new user on the basis of the biometric data.

Figure 4:
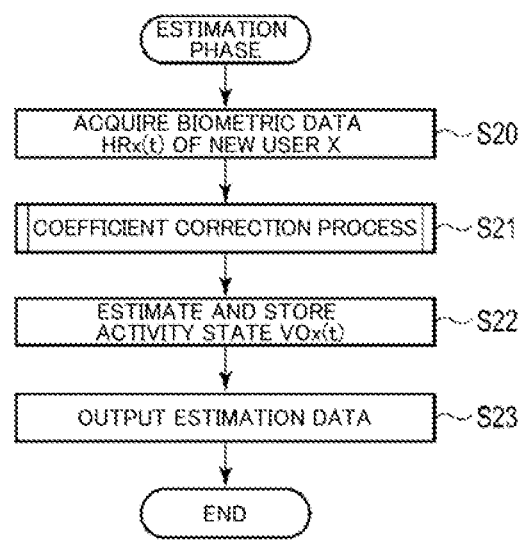
FIG. 4 is a flowchart illustrating the procedure and the content of the processing in an estimation phase by the state estimation device illustrated in FIG. 1.

FIG. 4 is a flowchart illustrating the procedure of an estimation process. Now it is assumed that, in a state in which a new user x measures his or her biometric data using a measurement apparatus and the measurement data HRx(t) is stored in the user terminal 2x, the user x performed an operation for requesting the state estimation device 1 for estimation of the activity state. By doing so, the measured biometric data HRx(t) of the user x is transmitted from the user terminal 2x to the state estimation device 1 via the network 3.

In step S20, the state estimation device 1 receives the biometric data HRx(t) transmitted from the user terminal 2x with the aid of the communication interface unit 30 and delivers the received biometric data HRx(t) to the coefficient correction processing unit 105 under the control of the biometric data acquisition unit 104.

Figure 5:
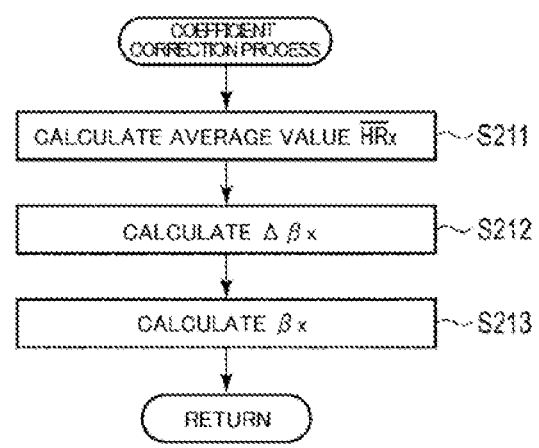
FIG. 5 is a flowchart illustrating the procedure and the content of a coefficient correction process in the estimation phase illustrated in FIG. 4.

In step S21, the state estimation device 1 executes a coefficient correction process as follows so that the coefficient of the regression model formula has a value corresponding to the new user x under the control of the coefficient correction processing unit 105. FIG. 5 illustrates an example of the processing procedure and the processing content.

That is, first, in step S211, the coefficient correction processing unit 105 calculates the average value $HRx^-$ of the biometric data HRx(t) of the new user x. Subsequently, in step S212, the coefficient correction processing unit 105 calculates a difference $\Delta \beta x$ of the coefficients on the basis of Formula (4) stored in the regression model formula storage unit 203. In step S213, the coefficient correction processing unit 105 calculates a coefficient $\beta x$ corresponding to the new user x on the basis of Formula (3) stored in the regression model formula storage unit 203.

Subsequently, in step S22, the state estimation device 1 corrects the coefficient $\beta$ in Formula (1) stored in the regression model formula storage unit 203 to the coefficient $\beta x$ corresponding to the new user x under the control of the estimation processing unit 106. Moreover, the state estimation device 1 calculates an activity state (exercise intensity) VOx(t) at time t of the new user x by substituting the biometric data HRx(t) of the new user x in Formula (2) in which the coefficient is corrected and stores the calculated activity state (exercise intensity) VOx(t) of the new user x in the estimation data storage unit 204 in correlation with the user ID.

Finally, in step S23, the state estimation device 1 transmits information representing the activity state (exercise intensity) VOx(t) of the new user x stored in the estimation data storage unit 204 from the communication interface unit 30 to the requesting user terminal 2x under the control of the estimation data output unit 107. An email, for example, is used as a transmission means. The user x may browse his or her activity state (exercise intensity) VOx(t) by accessing the web of the state estimation device 1 using a browser of the user terminal 2x.

(Effects)

As described hereinabove, in an embodiment, in the learning phase, the activity state data VOi(t) when a prescribed exercise is performed and the biometric data HRi(t) at that time are acquired from the user terminals 21 to 2N of a plurality of users, a regression formula representing the relationship between the HRi(t) and the activity state data VOi(t) is generated using a regression analysis method on the basis of these pieces of measurement data, the difference $\Delta\beta i$ between the coefficients of the regression formula of all users and each user is calculated, and a coefficient correction regression formula representing the relationship between the difference $\Delta\beta i$ of the coefficient and the average value $\overline{HRi}$ of the biometric data is generated. In the estimation phase, the biometric data HRx(t) of the new user x is acquired, the coefficient value $\beta$ of the activity state estimation regression formula is corrected to the coefficient value $\beta x$ for the new user x on the basis of the average value $\overline{HRx}$ of the biometric data and the coefficient correction regression formula, and the activity state of the new user x is estimated using the regression formula having the corrected coefficient.

Therefore, according to an embodiment, even when the biometric data of the new user x is outside an average range of users, since the coefficient of the regression formula is corrected on the basis of the biometric data of the new user x, it is possible to estimate the activity state of the new user x with high accuracy. Moreover, since the activity state is estimated using the learned regression formula, it is not necessary to measure the activity states of users directly, and it is possible to recognize the activity states of users without preparing large-scale equipment and an expensive measurement apparatus.

Other Embodiment

In the embodiment, although a case of measuring heart rates as the biometric data and estimating an exercise intensity as the activity state data has been described as an example, there is no limitation thereto. For example, as described above, a blood pressure, a blood-sugar level, or the like may be measured as the biometric data, and a test value measured by a general test such as a blood test or a urine test may be used. Moreover, a step count measured by a pedometer, a moving distance measured by a GPS sensor, and the like may be used as the biometric data. On the other hand, beside the exercise intensity, a maximum oxygen intake, a measurement value obtained by an activity meter, the survey data of subjective symptoms, a fatigue level measured by a measurement apparatus such as a flicker tester, and a mental state such as stress may be measured as the activity state data.

As described above, rather than providing the functions of the state estimation device 1 in a web server or a cloud server, the functions may be provided in the terminal of a medical worker such as a doctor or a nurse or a health manager such as a public health nurse or may be provided in the user terminal itself. Moreover, the functions of the state estimation device 1 (for example, a learning function and an estimation processing function) may be distributed to a plurality of servers and terminals.

While the embodiment of the present invention has been described in detail, the above description is only an example of the present invention in all respects. Naturally, various improvements and modifications can be made without departing from the spirit of the present invention. That is, when the present invention is embodied, a specific configuration corresponding to an embodiment may be employed appropriately.

This invention is not limited to the embodiment as it is but can be embodied by modifying components in the practical phase without departing from the gist thereof. Moreover, it is possible to form various inventions by appropriately combining a plurality of components disclosed in the embodiment. For example, some components can be removed from all components illustrated in the embodiment. Furthermore, the components in different embodiments may be suitably combined with each other.

REFERENCE SIGNS LIST

1 State estimation device
21 to 2N, 2x User terminal
3 Network
10 Control unit
20 Storage unit
30 Communication interface unit
101 Learning biometric data acquisition unit
102 Learning activity state data acquisition unit
103 Regression model formula generation unit
104 Estimation biometric data acquisition unit
105 Coefficient correction processing unit
106 Estimation processing unit
107 Estimation data output unit
201 Biometric data storage unit
202 Activity state data storage unit
203 Regression model formula storage unit
204 Estimation data storage unit

The invention claimed is:

1. An state estimation device comprising:
a processor; and
a storage medium having computer program instructions stored thereon, when executed by the processor, perform to:
acquires an index value representing an activity state of each of a plurality of users and biometric data measured in a period in which the activity is performed; generates a first regression formula representing a relationship between all pieces of biometric data and all index values for the plurality of users on the basis of the acquired biometric data and the acquired index value representing the activity state, generates a second regression formula representing a relationship between the biometric data and the index value for each of the plurality of users, and generates a third regression formula representing a relationship between an average of all pieces of biometric data of the plurality of users and a difference between coefficient values included in the first and second regression formulas; wherein the storage medium stores the generated first, second, and third regression formulas.

2. The state estimation device according to claim 1, further comprising: a second acquisition unit that acquires biometric data of an estimation target user; a coefficient correction unit that calculates a difference of a coefficient value corresponding to the acquired biometric data of the estimation target user on the basis of the stored third regression formula and calculates a corrected coefficient value corresponding to the estimation target user from the difference of the coefficient value and the coefficient value of the first regression formula; an estimation unit that estimates an index value of an activity state corresponding to the acquired biometric data for the estimation target user on the basis of the second regression formula in which the corrected coefficient value is applied; and an estimation data output unit that outputs the estimated index value of the estimated activity state to the estimation target user.

3. The state estimation device according to claim 1, wherein the index value representing the activity state represents an exercise intensity of a user in a certain period, and the biometric data represents a heart rate in the certain period.

4. An state estimation method executed by an information processing device having a processor and a storage medium, the method comprising: acquiring an index value representing an activity state of each of a plurality of users and biometric data measured in a period in which the activity is performed;

generating a first regression formula representing a relationship between all pieces of biometric data and all index values for the plurality of users on the basis of the acquired biometric data and the acquired index value representing the activity state, generating a second regression formula representing a relationship between the biometric data and the index value for each of the plurality of users, and generating a third regression formula representing a relationship between an average of all pieces of biometric data of the plurality of users and a difference between coefficient values included in the first and second regression formulas; storing the generated first, second, and third regression formulas in the storage medium.

5. The state estimation method according to claim 4, further comprising: acquiring biometric data of an estimation target user; calculating a difference of a coefficient value corresponding to the acquired biometric data of the estimation target user on the basis of the stored third regression formula and calculating a corrected coefficient value corresponding to the estimation target user from the difference of the coefficient value and the coefficient value of the first regression formula; estimating an index value of an activity state corresponding to the acquired biometric data for the estimation target user on the basis of the second regression formula in which the corrected coefficient value is applied; and outputting the estimated index value of the estimated activity state to the estimation target user.

6. A program for causing a processor included in the state estimation device to execute processing of the respective units included in the state estimation device according to claim 1.

* * * * *